United States Patent [19]
Bergersen

[11] 3,967,379
[45] July 6, 1976

[54] PREFORMED ANTERIOR LABIAL RETAINER

[76] Inventor: Earl O. Bergersen, 950 Linden Ave., Winnetka, Ill. 60093

[22] Filed: Dec. 18, 1974

[21] Appl. No.: 534,095

[52] U.S. Cl. .............................................. 32/14 B
[51] Int. Cl.² ............................................ A61C 7/00
[58] Field of Search ............... 32/14 R, 14 B, 14 A, 32/14 F; 128/136

[56] References Cited
UNITED STATES PATENTS
3,259,129   7/1966   Tepper ........................... 32/14 B X FOREIGN PATENTS OR APPLICATIONS
1,293,946   4/1969   Germany .......................... 32/14 F

OTHER PUBLICATIONS
"Rocky Mountain Gen. Cat.," Rocky Mountain Metal Prod. Co., p. 66, Mar. 20, 1956.
"Unitek Catalog No. 113", Unitek Corp., pp. 44 and 45, May 25, 1964.
*Notes on Dental Materials*, Combe, Churchill Livingstone, Edinburg, 1972, pp. 187–200.

Primary Examiner—Louis G. Mancene
Assistant Examiner—Jack Q. Lever
Attorney, Agent, or Firm—Larson, Taylor and Hinds

[57] ABSTRACT

A retainer comprising a portion located against the lingual tooth and tissue surfaces for holding a wire against the labial surfaces of the anterior teeth, which is known as a Hawley Retainer, is preformed as a molded piece of a shape and of a material permitting fitting to a patient by a method which includes reshaping of the preform directly in the mouth of the patient, thereby eliminating the need to first form a cast of the patient's teeth. Several preforms of different sizes form a set which will fit mouth sizes of substantially the entire dental patient population. The material is designed to soften for non-elastic manipulation against the lingual surfaces at a temperature above body temperature but below that temperature at which the tissues within the patient's mouth would burn.

63 Claims, 28 Drawing Figures

PREFORMED ANTERIOR LABIAL RETAINER

BACKGROUND OF THE INVENTION

This invention relates to the field of orthodontics, and in particular it concerns improvements relating to the type of retainer adapted to locate a wire against the labial surfaces of the upper or lower anterior teeth, which retainer is commonly referred to as a "Hawley Retainer".

In the overall process of effecting straightening of a child's teeth, a point is reached at which the teeth themselves have been completely straightened, whereupon the straightening appliances such as braces or the like are removed and a retainer such as a Hawley Retainer is utilized for urging the straightened teeth into a final position. At the present time, the procedure for making this retainer is as follows. Firstly, an impression of the teeth is made, from which is molded a plaster of paris model of the patient's teeth. A wire is then shaped and adapted to the model. The model is then coated with a separating medium and the wire is glued to the model. A self-cure acrylic methyl methacrylate acrylic is then poured onto the model to the correct thickness. The retainer is then removed from the model, cleaned, and trimmed ready to be fitted to the patient's mouth. The retainer is then fitted to the mouth and the bite plane is adjusted to the correct position and then polished.

In an alternative, and in some ways more complicated procedure, instead of using the self-cure acrylic, a flat disc is either drawn by suction or pushed by fluid pressure onto the model of the patient's teeth. All suction procedures require the added complication of providing a suction means for cooperating therewith while some suction processes require the added complication of drilling suction holes through the model. The pressure procedures require the further complication of fixing the wire in place with self-cure acrylic so that it is not displaced during the forming process. In either event, forming such a custom retainer is quite time consuming in that it requires one to one and a half hours, approximately half of which is the orthodontists actual time, the other half comprising lab time. However, of perhaps greater significance is the fact that because of various other delays such as the time required for drying of the cast, it takes at least several days between the time that the orthodontic appliances are removed and the time that the completely fabricated custom made retainer can first be used. This represents a considerable disadvantage since relapse occurs almost immediately upon removal of the straightening appliances. It has been found for example that almost 30% of the relapses in overbite and overjet of finished cases occur within the first ten days following band removal. Hence, this delay of several days between band removal and the commencement of retainer use provides a significant opportunity for this type of relapse to occur. There is also psychological disadvantages resulting from this delay of several days in that the cooperation enthusiasm of the patient may well diminish during this delay while waiting for a custom retainer with nothing to wear in his mouth during this time.

Hence, there exists a need for improvements relating to a retainer of the type described which will reduce or eliminate the disadvantages existing in the present state of the art.

SUMMARY OF THE INVENTION

It is a purpose of this invention to provide improvements relating to anterior labial retainers of the type commonly referred to as Hawley Retainers which will overcome the problems and disadvantages existing in the prior art.

The achievement of this purpose of the present invention was made possible by the discovery that it was a possibility to design and produce a preform of a retainer of the present type which could be successfully formed into its final functional shape within the patient's mouth, thus bypassing the heretofore necessary task of first forming a model of the patient's mouth.

In accordance with a feature of the present invention, after extensive study and consideration of numerous factors relating to the oral anatomy of the patient, it was discovered that with just a small number of sizes, which sizes differ from each other in a specified manner, it was possible to fit essentially the entire dental patient population.

In accordance with one preferred embodiment of the present invention, there is provided a preform having a relatively thick forward portion having a front edge positionable adjacent the lingual surfaces of the anterior teeth and a rearward portion extending rearwardly therefrom and extending at least alongside the lingual tooth or tissue surfaces and adapted to be formed against these lingual surfaces during the process of shaping the preform to the shape of the patient's mouth.

A further feature of the present invention is the provision of a preform of a retainer of the type described which includes a labial wire embedded therein.

The procedure for fitting a patient with a retainer of the present type comprises taking a preform of a proper size for the particular patient, inserting it into the patient's mouth and against the lingual surfaces to non-elastically reshape the device to fit at least in part against some of the lingual surfaces for retaining the device in the mouth of the wearer with the labial wire against the labial surfaces of the anterior teeth. Preferably the preform is of a material which softens at a temperature well above body temperature but below a temperature which would burn the patient's mouth, the material becoming sufficiently soft at these said temperatures to be easily reshaped to the contours of the lingual surfaces of the patient's mouth without unnecessary discomfort to the patient. The material would of course have the further characteristic of again becoming too stiff for easy manual reshaping when it cools down to body temperature.

Thus, it is an object of the present invention to provide substantial improvements in the art relating to Hawley Retainers.

It is still another object of this invention to provide improvements in the art relating to Hawley Retainers which obviates the need to make a cast model of the patient's mouth in the step of fitting a retainer to the patient.

It is still another object of this invention to provide a preformed retainer of the type described, i.e. preformed prior to any contact with the mouth of any patient or representation thereof which is adapted to be placed onto a patient's mouth and shaped therein to its final functional shape.

It is still another object of this invention to provide a preform as described in the preceding paragraph including a labial wire embedded therein.

It is still another object of this invention to provide a set of a limited number of preformed retainers of differing sizes which will fit substantially the entire dental patient population.

It is still another object of this invention to provide a preform retainer adapted to be fitted directly to a patient without the use of a model of the patient or the like, which preform is of a material which will become sufficiently soft for reshaping purposes at a temperature above body temperature but below a temperature at which the patient's mouth would burn, and which again becomes stiff upon cooling to body temperature.

It is still another object of the present invention to provide a method for fitting a patient with a retainer of the type described which comprises taking a preform thereof and without the use of any model or other representation of the patient's mouth, shaping the preform to the patient by placing it within the patient's mouth and reshaping it directly to the contours of the patient's mouth while located therein.

It is still another object of the present invention to provide a method for fitting a preform retainer as described in the preceding paragraph wherein the preform is of a material which becomes soft at a temperature above body temperature but below a temperature at which the patient's mouth would burn, whereby the step of shaping the preform to the contours of the patient's mouth comprises first heating the preform to the softening temperature and then shaping it to the contours of the patient's mouth while located therein.

These and other objects of the present invention will become apparent from the following detailed description of the preferred embodiments of the present invention, taken together with the accompanying drawings.

BRIEF DESCRIPTION OF THE DRAWINGS

There follows a detailed description of preferred embodiments of the present invention which are to be read together with the accompanying drawings which are provided for the purpose of illustrating preferred embodiments of the invention.

FIG. 1 is a sectional view through a central sagittal plane of a patient's mouth showing a preformed retainer constructed in accordance with the present invention, adapted and positioned within a patient's mouth.

FIGS. 2A and 2B illustrate in front perspective view a preformed retainer constructed in accordance with the present invention, wherein FIG. 2A illustrates the retainer in its original preformed shape and FIG. 2B illustrates this same retainer after it has been shaped to the mouth of a specific patient.

FIG. 17 is a plan view of a preformed retainer constructed in accordance with the present invention and illustrating certain modifications.

FIG. 18 is a vertical, coronal sectional view taken along line 18—18 of FIG. 17.

DETAILED DESCRIPTION OF THE PREFERRED EMBODIMENTS

Referring now to the drawings, like elements are represented by like numerals throughout the several views.

Figures 1, 2A, 2B, 17, 18:
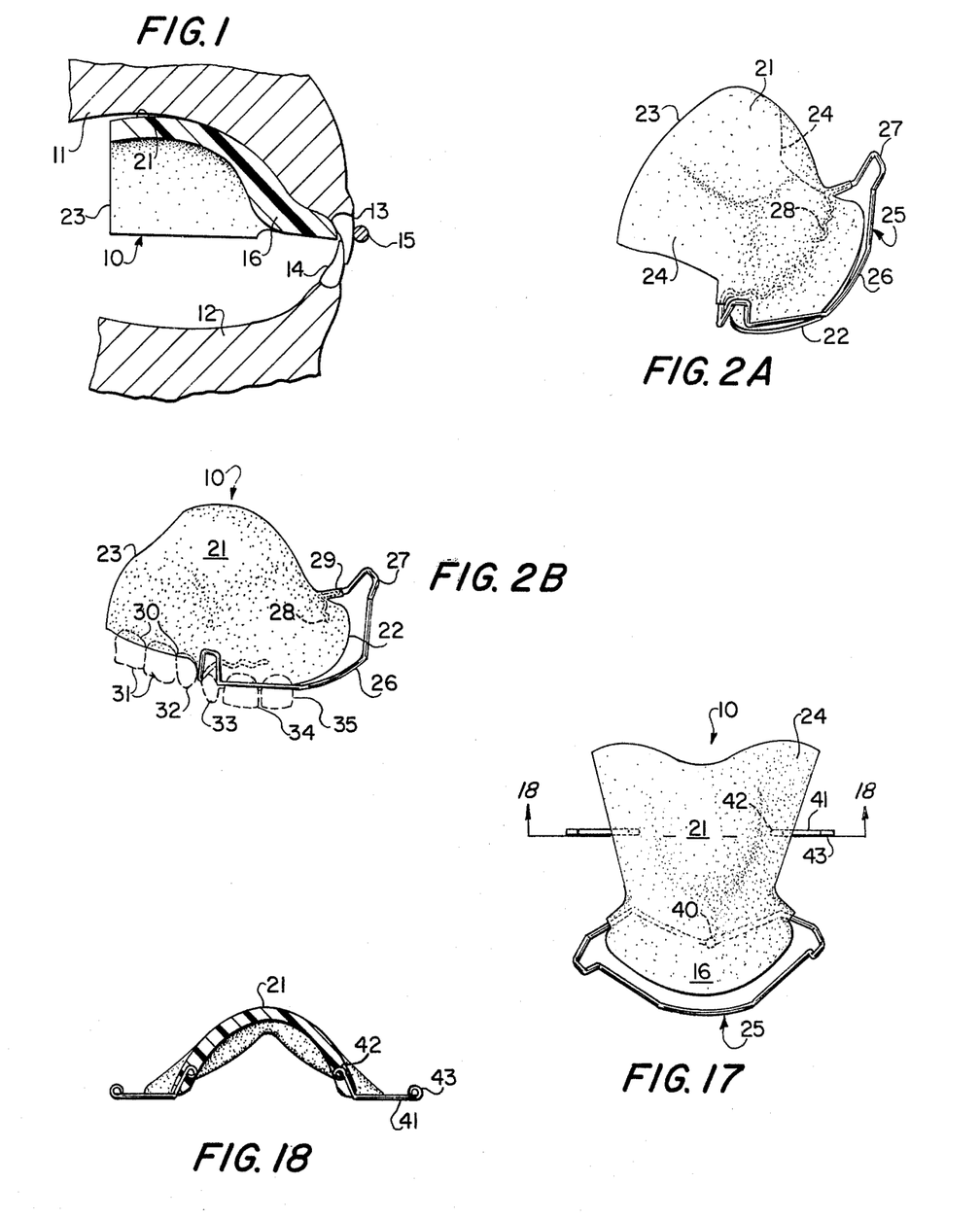

Although the important features of the present invention will be described in significantly greater detail below, for a basic understanding of the invention reference is made to FIGS. 1, 2A and 2B, wherein FIG. 2A illustrates a preform constructed in accordance with the features of the present invention, FIG. 2B illustrates that same preform after it has been fitted to a patient so that it is actually a finished retainer and FIG. 1 illustrates the retainer of FIG. 2B within the patient's mouth.

There is shown in these drawings the retainer 10 which, as noted above, is generally referred to as a "Hawley Retainer". Referring to FIG. 1, the retainer is shown in place against the palate 11 of the patient's mouth. Since this is a central sagittal view, the teeth 13 and 14 would be the upper and lower left central incisor, respectively, the floor of the patient's mouth being represented at 12. The retainer includes a labial wire 25 located against the labial surfaces of the upper anterior teeth. The top 21 and the open posterior 23 of the retainer 10 are also shown in FIG. 1.

Referring to FIG. 2A, the preform includes a top 21, a front edge 22, the posterior 23 and lateral sides 24. The horizontal labial wire 25 comprises a front arch 26, a pair of vertically extending gingival loops 24 which at their outer ends turn horizontally and enter the interior of the preform where they are anchored as shown at 28. This portion of the preform rearward of the front edge which receives the ends of the wire is considerably thickened relative to the remainder of the preform as shown at 16 in FIG. 1.

As indicated above, FIG. 2B illustrates the preform of FIG. 2A after it has been finally fitted to the mouth of a specific patient. The top 21, the front portions 16 and 22 and the wire 25 have been essentially reshaped to adapt to the contours of the patient's mouth while the sides 24 have been cut away at parts and formed with interproximal protrusions 30. The right-hand teeth are shown in dotted lines in FIG. 2B and it is to be understood that the retainer 10 is symmetrical so that the side thereof not illustrated would fit with respect to the left side of the patient's mouth in a manner identical to that shown in FIG. 2B for the right side of the mouth. As shown therein, interproximal points 30 protrude between the molars 31 and between the first molar and the bicuspid tooth 32. The wire 25 crosses from the labial to the lingual side of the teeth between the bicuspid 32 and the canine tooth 33. The wire is shown against the front right incisor teeth 34 and 35.

The development of and the basic and critical features of the present invention will now be described in detail with respect to FIGS. 3 through 11.

Before approaching the task of providing preformed retainers, and preferably a set thereof, it was recognized that each patient's mouth is somewhat unique both as to size and shape. It was not apparent that a limited number of sizes could be made to accommodate the differences in the sizes of patient's mouths; and it was of course even less apparent that a limited number of retainer sizes could accommodate the numerous different shapes of patient's mouths, much less the combination of differences in patient's mouth sizes and shapes. Compounding these difficulties are the limitations in existing synthetic materials considered in the context of the sharp contours within a patient's mouth. When fitting a retainer to a model of a patient's mouth, one may of course apply very great pressures and at very high temperatures; but in contrast thereto, when working within a patient's mouth, both the applied force and the working temperature conditions are severely limited.

The discussion which follows will describe the development of the invention specifically with reference to a maxillary arch Hawley Retainer. However, it will be understood that the features of the invention are equally applicable to a mandibular arch Hawley Retainer.

As a first step, average tooth size variations were determined on over 50,000 individuals to determine the limits of the population in regards to the cummulative mesio-distal widths of the upper six anterior teeth. As a result of this study it was determined that the teeth in this dimension vary by a total of 24.0 mm. while 95% of the population varies by 21.0 mm. As a result, this variation was divided into 3 mm. increments and seven individual sizes were disigned to fit 95% or two standard deviations of the population. Casts of patients for each of these seven individual sizes were measured in nine different dimensions to ascertain average palatal shapes and sizes, as well as average positions of individual teeth and arch shape. An average of ten casts for each size were analyzed and actual palatal shapes were then transferred to paper. These were then averaged and average palatal shapes in all nine dimensions for seven different sizes were designed.

These seven sizes each vary by 3 mm. in the mesio-distal dimension of the six upper anterior teeth starting with 42.5 mm. for the smallest size, (45.5, 48.5, 51.5, 54.5, 57.5 for the five intermediate sizes respectively), while the largest size is 60.5 mm.

In experimenting with prototypes of the plastic palatal piece without the wire attached to it, several important and unobvious principles of design were discovered. Referring to FIGS. 3–11, (1) the area of plastic between lines H and F bounded by lines left and right P, which is part of the thick part 16 referred to earlier, is important in that it does not distort under heat very well because of its thickness which, as will be explained below, is necessary to hold the wire ends. Therefore, it must be contoured quite accurately to fit the shallower palates in the sample. The same is true of that part of thick part 16 between I and H lateral to line P on each side for the same reason; (2) the contour of the palatal surface 21 posterior to these thickened areas 16 mentioned under (1) is easier to contour to the palate than around the teeth. It is however, quite painful to the patient if the material is too large or high for the soft tissue and an increase in pressure develops so that the material of 21 is pushed quite hard against the palate in order for it to be contoured correctly. On the other hand, if the plastic is too short from fitting it is also painful when it has to be pushed hard to properly contour it. As a result, the palatal area 21 posterior to line H between the two P lines were contoured to the mean palatal shape in the sample. In this way the plastic would have to be hand-molded to the palate the least amount whether the palatal contour would be high and vaulted, low and flat, narrow or wide; (3) the posterior sides 24 lateral to lines Q and posterior to line J are slightly wider than the average width in this area of the sample since if the plastic material exhibited any degree of a memory it would be better for it to expand in time than constrict. There also was a tendency for the plastic to curl up away from the palate when the side away from the palate (external or non-tissue surface) was trimmed with a finishing tool. Since there usually is a tendency to polish the non-tissue surface slightly this expansion built into the palate would tend to counteract this possible trimming shrinkage; (4) the contour on the lingual surface of the six anterior teeth was quite variable as was the area 3 mm. lingual to this. In some cases the area in profile at right angles to the lingual surface of the tooth is convex and in others it is concave so the contour of the plastic was tapered considerably as it reached the surface of each tooth so that it could more easily be contoured to the lingual tooth surface; (5) the extra lower flange area of sides 24 in the posterior area extending inferiorly from the occlusal line to the free lateral margin was extended so that this extra material would compensate for highly vaulted palates. These longer lateral areas of plastic assure that the lingual surfaces of especially the first and second molars would be covered by plastic. As is seen in the sagittal drawings of FIGS. 9–11, this area 24 tapers so that the largest flange is opposite the molars where it is needed the most; (6) the shapes of each palate are quite uniform from one size to the next, the sizes of which vary only according to upper anterior tooth widths. When the contour varied from the average in experimental injection-molding dies that were not made to average-shaped palates, it was impossible to properly contour the heat-sensitive palate accurately so that it would fit without falling out. It was realized that a detailed study of palatal contour was necessary to get the plastic to fit as close as possible to the actual contour of the patient; (7) the heat-sensitive plastic to be molded in the mouth to fit the patient's palatal contours could not be placed against tissue when it was above a temperature of 190° F., and yet it could not distort as normal body temperature. Experimental plastics which molded well at 180° F., also distorted within one day at body temperature when worn by the patient, by curling away from the lingual surfaces of the posterior teeth. As a result, plastic that would be stiffer at all temperatures had to be used so that little distortion would occur at body temperature. These factors strongly limited the design possibilities since it precluded free and easy shaping of the plastics within the patient's mouth and required instead a much closer shaping of the preform to the shape of the patient's mouth which, of course, militated directly against the desired goal of fitting as many people as possible with a single preform. This further required extreme accuracy in the design and injection molding of the retainer so that the palate 21 would fit as accurately as possible to the average palatal contour. In this way the least amount of hand molding would be necessary to create a proper fit.

Another major problem was that of the shape and size of the labial wire segment 25. Having found that plastic retainer parts could be provided which each fit a small range of sizes, how could one now apply to it a wire segment which requires a more perfect fit for each patient? Heretofore the wire segments had always been custom fitted to the individual patient. The adaptation of the wire 25 to the labial contour of the arch from the one canine to the other involved measuring the widths of the teeth and also charting the average surface contour in a similar manner to that by which the palate 21 was analyzed. From the general curvature in the area of the central incisors it was statistically determined that the wire 25 could have the same radius of curvature on all sizes. The radius was established by the curvature of the median size from all the seven sizes. The bend 36 (FIG. 3) for the lateral incisor inset at line U of FIG. 3 was calculated to occur at the average mesial interproximal area for the lateral incisor of each of the seven sizes. The vertical gingival bend 27 in the wire at line V occurs at the proper position if it is 10.0 mm. mesial to line W along the curvature of the same radius (0.868 inch) of the central incisors.

The vertical gingival loop 27 between lines V and W are preferably tapered buccally 20° from the vertical to accommodate extreme buccal taper of the gingival tissue of the basal bone area. This taper prevents the gingival loop from abrading or injuring the tissue by being too close to the tissue. The length of this loop 27 also was tested so as not to impinge into the sulcus between the cheek and basal bone area of any of the cases studied. If the loop is too long it will perforate the soft tissue in the mouth when the retainer is worn.

The wire part 29 entering through the canine bicuspid interproximal along line W is to be slightly gingival to the occlusal plane when it actually enters the plastic piece part so that it has an equal amount of plastic both occlusal and gingival to the wire, so that the wire does not pull out of the plastic when it is warmed. The same is true for the small anchored end 28 of the wire that runs along line Y to the very center of the thick portion 16 of the plastic and preferably to the thickest part thereof.

Figures 3, 4, 5:
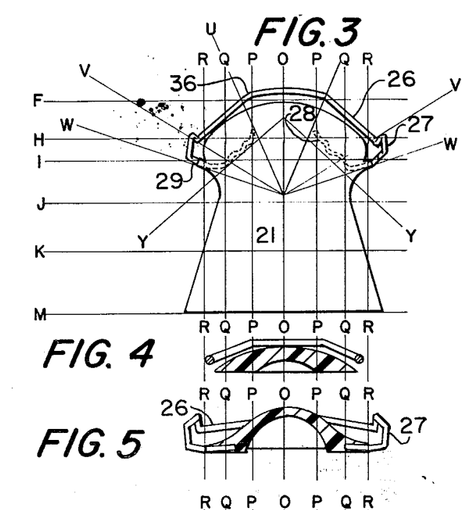
FIG. 3 is a plan view of the preformed retainer of the present invention with lettered lines drawn thereon for use in relating this figure to subsequent FIGS. 4 through 11 and also for relating this illustration of the invention to the tables of dimensions set forth later in the specification.
FIG. 4 is a vertical coronal sectional view taken along line H—H of FIG. 3.
FIG. 5 is a vertical, coronal sectional view taken along line I—I of FIG. 3.
Figure 6:
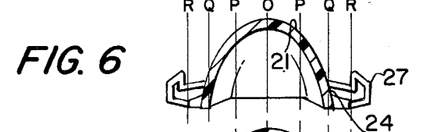
FIG. 6 is a vertical, coronal sectional view taken along line J—J of FIG. 3.
Figures 7, 8:
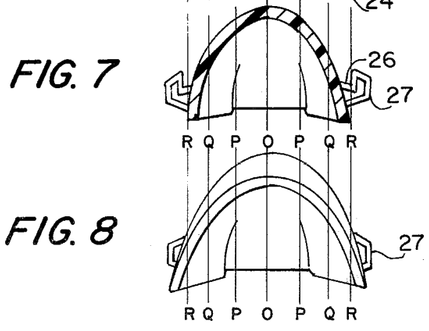
FIG. 7 is a vertical, coronal sectional view taken along line K—K of FIG. 3.
FIG. 8 is a posterior elevational view, taken along line M—M of FIG. 3.
Figure 9:
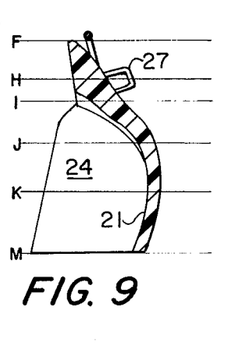
FIG. 9 is a vertical sagittal sectional view taken along line O—O of FIG. 3.
Figure 10:
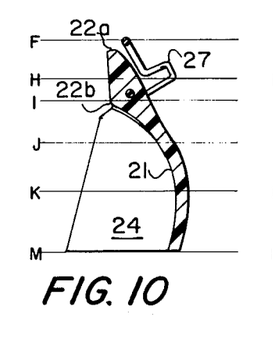
FIG. 10 is a vertical sagittal sectional view taken along line P—P of FIG. 3.
Figure 11:
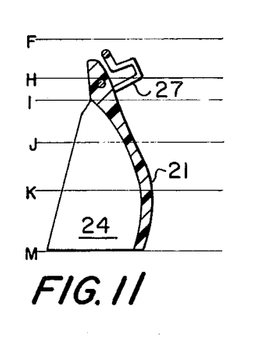
FIG. 11 is a vertical sagittal sectional view taken along line Q—Q of FIG. 3.

The portion of the bent wire at the junction of loop 27 and part 29, i.e. in the area of the intersection of lines W and I of FIG. 3 extends laterally outwardly beyond the wire curvature of radius 0.898 inch by 1 mm. This compensates for variable cuspid-to-cuspid dimensions, especially those that are more excessive than the average.

The shape of the wire is important since the wire holds the labial surface of the teeth in the mouth. If it is of the wrong configuration naturally it will move teeth in the wrong position. Tissue impingement has already been mentioned; however, it is quite serious since permanent damage in the form of perforation or detachment of tissue from the root can occur if proper clearance is not made.

Of technical importance, each wire for each size has to be made perfectly to fit into its receptacle in the die of the injection mold. Otherwise it would be impossible to properly mold the part. Also, if the wire has to be distorted to fit into the die mold, then when the plastic is heated to be fitted by hand into the mouth, it will distort the warmed plastic and make it difficult to work with in the mouth.

The preceding discussion has mentioned that a set of eight different preforms would fit essentially the entire dental patient population. For economical reasons, however, it is preferable to design seven sizes which would fit essentially 95% of the dental patient population. These seven sizes and their relationship to the width of the six upper anterior teeth have been mentioned earlier in this discussion. However, considering all of the numerous factors which have been mentioned above and considering FIGS. 3 through 11, the specific dimensions of these seven sizes would be as follows:

Table I

| Retainer Size | Angular Relations (Plastic and Wire) Angles | | | |
|---|---|---|---|---|
| | O-J-W | O-J-V | O-J-U | V-J-W |
| 2 | 57.17 | 44.19 | 21.0 | 12.98 |
| 3 | 61.20 | 48.22 | 21.0 | 12.98 |
| 4 | 65.24 | 52.26 | 22.0 | 12.98 |
| 5 | 69.27 | 56.29 | 25.0 | 12.98 |
| 6 | 73.31 | 60.33 | 28.0 | 12.98 |
| 7 | 77.34 | 64.36 | 31.0 | 12.98 |
| 8 | 81.38 | 68.40 | 34.0 | 12.98 |

Table II

Radii of Circular Arcs (Plastic and Wire)

| | Radius of all Sizes in Inches |
|---|---|
| A. Labial Surface of Wire | .898 |
| B. Lingual Surface of Wire | .868 |
| C. Labial Arc of Die | .809 |
| D. Midway B and C | .8385 |

Table III

Circumferences of Arcs (Plastic and Wire)

| Retainer Size | W-W (D Radius .8385) mm. | inches | W-W (B Radius .868) mm. | inches | V-V (B Radius .868) mm. | inches |
|---|---|---|---|---|---|---|
| 2 | 42.5 | 1.67 | 44.05 | 1.73 | 34.05 | 1.34 |
| 3 | 45.5 | 1.79 | 47.15 | 1.86 | 37.15 | 1.46 |
| 4 | 48.5 | 1.91 | 50.26 | 1.98 | 40.26 | 1.58 |
| 5 | 51.5 | 2.03 | 53.37 | 2.10 | 43.37 | 1.71 |
| 6 | 54.5 | 2.15 | 56.48 | 2.22 | 46.48 | 1.83 |
| 7 | 57.5 | 2.26 | 59.59 | 2.35 | 49.59 | 1.95 |
| 8 | 60.5 | 2.38 | 62.70 | 2.47 | 52.70 | 2.07 |

Table IV

Dimensions Between Base Lines in mm. (Horizontal Occlusal Plane)

| Retainer Size | F-H | F-I | F-J | F-K | F-M | F-M' | O-P | O-Q | O-R |
|---|---|---|---|---|---|---|---|---|---|
| 2 | 5.8 | 9.6 | 18.8 | 27.3 | 39.6 | — | 7.7 | 12.6 | 17.1 |
| 3 | 6.2 | 10.4 | 20.0 | 29.1 | 41.8 | — | 7.7 | 12.6 | 17.1 |
| 4 | 7.3 | 11.6 | 20.9 | 31.0 | 44.0 | — | 7.7 | 12.6 | 17.1 |
| 5 | 8.9 | 12.9 | 21.7 | 33.0 | 45.8 | — | 7.7 | 12.6 | 17.1 |
| 6 | 10.4 | 14.8 | 22.2 | 35.1 | 47.9 | — | 7.7 | 12.6 | 17.1 |
| 7 | 11.6 | 15.7 | 23.2 | 31.0 | 41.8 | 45.6 | 717 | 12.6 | 17.1 |
| 8 | 12.2 | 17.1 | 24.4 | 33.0 | 44.0 | 47.8 | 7.7 | 12.6 | 17.1 |

M' = Posterior termination of retainer.

Table V

Palatal Measurements (Plastic Piece-Part)
Length of Retainer (Plastic) in mm.
(Horizontal Occlusal Plane)

| Retainer Size | O | P | Q | R |
|---|---|---|---|---|
| 2 | 39.1 | 37.2 | 34.5 | 8.9* |
| 3 | 41.8 | 40.0 | 36.8 | 10.3* |
| 4 | 43.8 | 42.4 | 40.2 | 12.2* |
| 5 | 46.1 | 44.6 | 42.1 | 36.7 |
| 6 | 47.7 | 46.4 | 42.8 | 37.8 |
| 7 | 45.2 | 43.8 | 40.9 | 36.1 |
| 8 | 47.6 | 46.0 | 43.3 | 39.1 |

*Line R only measurable in posterior portion of plastic.

Table VI

Width of Retainer (Plastic) in mm.
(Horizontal Occlusal Plane)

| Retainer Size | H | I | J | J4N | K | M | M' |
|---|---|---|---|---|---|---|---|
| 2 | 24.4 | 24.6 | 25.6 | 26.9 | 31.4 | 39.8 | — |
| 3 | 25.0 | 24.8 | 26.3 | 27.0 | 32.4 | 41.0 | — |
| 4 | 26.0 | 25.0 | 26.8 | 26.8 | 33.4 | 42.0 | — |
| 5 | 26.5 | 25.5 | 27.8 | 27.1 | 35.6 | 42.8 | — |
| 6 | 27.1 | 25.9 | 27.8 | 27.1 | 35.7 | 43.4 | — |
| 7 | 27.5 | 27.4 | 26.5 | 26.1 | 32.2 | 41.2 | 44.0 |
| 8 | 27.5 | 27.4 | 26.5 | 26.1 | 32.2 | 41.2 | 44.0 |

M' = Posterior termination of retainer.

Table VII

Height of Retainer (Plastic) in mm.
(Coronal Plane) at O Line
Measured from Occlusal Line Superiorly to Tissue Surface

| Retainer Size | H | I | J | K | M | M' |
|---|---|---|---|---|---|---|
| 2 | 3.1 | 4.9 | 13.2 | 15.3 | 12.9 | — |
| 3 | 3.3 | 5.5 | 13.9 | 17.2 | 14.0 | — |
| 4 | 4.2 | 8.0 | 14.7 | 17.2 | 14.8 | — |
| 5 | 4.4 | 7.9 | 15.2 | 18.0 | 14.9 | — |
| 6 | 4.5 | 7.9 | 16.4 | 18.7 | 15.7 | — |
| 7 | 5.2 | 8.3 | 16.0 | 18.7 | 17.5 | 16.5 |
| 8 | 5.0 | 8.2 | 16.6 | 19.6 | 17.7 | 15.8 |

Measured from Occlusal to Most Inferior Section

| Retainer Size | H | I | J | K | M | M' |
|---|---|---|---|---|---|---|
| 2 | 1.5 | 0 | 9.0 | 10.3 | 12.3 | — |
| 3 | 1.5 | 0 | 8.9 | 10.2 | 12.3 | — |
| 4 | 1.5 | 0 | 8.8 | 10.7 | 12.3 | — |
| 5 | 0 | 0 | 8.5 | 10.4 | 12.3 | — |
| 6 | 0 | 0 | 8.4 | 10.7 | 12.5 | — |
| 7 | 0 | 0 | 8.4 | 9.5 | 11.1 | 11.4 |
| 8 | 0 | 0 | 8.3 | 9.6 | 11.0 | 11.4 |

M' = Posterior termination of retainer.

Table VIII

Height of Retainer (Plastic) in mm.
(Coronal Plane) at P Line
Measured from Occlusal Line Superiorly to Tissue Surface

| Retainer Size | H | I | J | K | M | M' |
|---|---|---|---|---|---|---|
| 2 | 1.9 | 2.8 | 8.5 | 12.3 | 11.4 | — |
| 3 | 2.2 | 3.2 | 10.9 | 14.6 | 12.8 | — |
| 4 | 3.3 | 4.1 | 10.2 | 14.7 | 13.5 | — |
| 5 | 2.8 | 4.2 | 11.5 | 15.6 | 13.6 | — |
| 6 | 2.8 | 4.2 | 12.7 | 16.3 | 14.5 | — |
| 7 | 3.4 | 4.1 | 11.0 | 16.0 | 14.8 | 13.4 |
| 8 | 3.7 | 4.4 | 11.4 | 15.5 | 14.6 | 13.4 |

Measured from Occlusal to Most Inferior Section

| Retainer Size | H | I | J | K | M | M' |
|---|---|---|---|---|---|---|
| 2 | 1.5 | 1.5 | 8.6 | 10.0 | 12.0 | — |
| 3 | 1.5 | 0.9 | 8.6 | 10.4 | 12.4 | — |
| 4 | 1.5 | 0.8 | 8.5 | 10.5 | 12.4 | — |
| 5 | 1.5 | 0 | 8.6 | 10.5 | 12.5 | — |
| 6 | 1.5 | 0 | 8.4 | 10.5 | 12.3 | — |
| 7 | 1.5 | 0 | 7.9 | 9.3 | 10.9 | 11.2 |
| 8 | 1.5 | 0 | 8.0 | 9.6 | 11.0 | 11.2 |

M' = Posterior termination of retainer.

Table IX

Height of Retainer (Plastic) in mm.
(Coronal Plane) at Q Line
Measured from Occlusal Line Superiorly to Tissue Surface

| Retainer Size | H | I | J | K | M | M' |
|---|---|---|---|---|---|---|
| 2 | -.5* | 0 | 1.7 | 7.2 | 7.8 | — |
| 3 | -.7* | 1.4 | 3.6 | 8.3 | 7.8 | — |
| 4 | 0 | 1.4 | 5.1 | 9.2 | 8.9 | — |
| 5 | 1.0 | 2.0 | 5.6 | 10.3 | 10.0 | — |
| 6 | 1.3 | 2.3 | 5.7 | 12.1 | 11.0 | — |
| 7 | 0.9 | 1.8 | 2.9 | 7.9 | 10.7 | 10.5 |
| 8 | 1.3 | 1.9 | 3.2 | 8.4 | 11.1 | 10.5 |

Measured from Occlusal to Most Inferior Section

| Retainer Size | H | I | J | K | M | M' |
|---|---|---|---|---|---|---|
| 2 | 1.5 | 1.5 | 8.1 | 9.0 | 11.2 | — |

Table IX-continued

| 3 | 1.5 | 1.5 | 8.6 | 9.8 | 12.0 | — |
| 4 | 1.5 | 1.5 | 8.4 | 10.0 | 12.1 | — |
| 5 | 1.5 | 0.5 | 8.5 | 10.2 | 12.1 | — |
| 6 | 1.5 | 0.6 | 8.5 | 10.3 | 12.3 | — |
| 7 | 1.5 | 1.5 | 8.4 | 9.6 | 11.3 | 11.5 |
| 8 | 1.5 | 1.5 | 8.4 | 9.7 | 11.5 | 11.7 |

M¹ = Posterior termination of retainer.
*Inferior to occlusal line.

Table X

Width of Retainer (Plastic) in mm. at Horizontal Plane

| Retainer Size | H* | I* | J** | K** | M** |
| --- | --- | --- | --- | --- | --- |
| 2 | 27.7 | 29.7 | 31.1 | 41.1 | 50.6 |
| 3 | 28.8 | 30.0 | 31.1 | 41.1 | 50.6 |
| 4 | 31.5 | 32.1 | 31.1 | 41.1 | 50.6 |
| 5 | 33.8 | 32.6 | 31.3 | 42.6 | 51.5 |
| 6 | 35.7 | 31.2 | 31.3 | 42.6 | 51.5 |
| 7 | 36.3 | 28.5 | 30.8 | 39.5 | 50.9 |
| 8 | 36.3 | 28.5 | 30.8 | 39.5 | 50.9 |

*At level of bite-plane 1.5 mm. inferior to occlusal line.
**At level of X line.

The procedure for fitting a patient with a preformed retainer as described above will be desscribed shortly in detail, especially with reference to photographic FIGS. 12A through 16B. However, reference is first made to FIGS. 17 through 25 which illustrate certain modifications and variations of the present invention.

FIGS. 17 and 18 illustrate a maxillary preform prior to fitting and hence essentially the same as shown in FIGS. 2A and 3 through 11. In this instance, however, certain variations are shown. Firstly, in place of the wavy configuration shown at 28 in the earlier embodiment the wire 25 is soldered at 40 to form essentially a closed loop with the ends of the wire at the solder 40 located within the thick portion 16 of the retainer 10. Secondly, the retainer is formed with a posterior wire 41 having a first looped end 42 within the lateral side 24 of the retainer. This wire 41 passes between the first and second molars and acts as a further clamp to hold the retainer in place, the outer loop 43 engaging the teeth at the gingival edges thereof. As another modification, the wire 25 can be designed as in FIG. 1 (not a closed loop) but with the ends of the wire formed with loops like the loops 42 rather than the wavy configuration of FIGS. 1-11.

FIGS. 19 through 22 illustrate a mandibular Hawley Retainer constructed in accordance with the features of the present invention. Like the maxillary preformed retainer, the mandibular retainer includes a thickened front portion 53 analogous to the thickened portion 16 for receiving the ends of the labial wire 51. As in the case of the maxillary device, the ends of wire 51 can be formed with loops like loops 42 of FIG. 17 or they can contact each other at a solder, like solder 40 of FIG. 17, located within the thickened portion 53 thereof. Rear wire clasps 52 similar in structure and function to the rear wire clasps 41 of FIGS. 17 and 18 can also be provided, except that the looped outer ends thereof would in this case pass through the interproximal of the first and second mandibular molars.

The procedure for fitting a patient with a preformed retainer as described with respect to FIGS. 1 through 11 will now be set forth, and for this purpose reference is made to photographic views 12A through 16B. Since each of views A and B are of the same specific item, in the following description the suffixes A and B will be dropped with respect to FIGS. 12 through 16.

Following the removal of all the orthodontic appliances from the patient's teeth, a measurement is taken of the mesio-distal width of the six upper anterior teeth either by measuring the teeth individually or with a measuring device that would measure the six teeth together and indicate the size retainer to be used. The sizes vary from No. 2 with a measurement of 42.5 mm. up through No. 8 with a measurement of 60.5 mm. Each retainer is designed to fit 3 mm. of variation above the millimetric size of the wire before the next size is indicated.

Figure 12A:
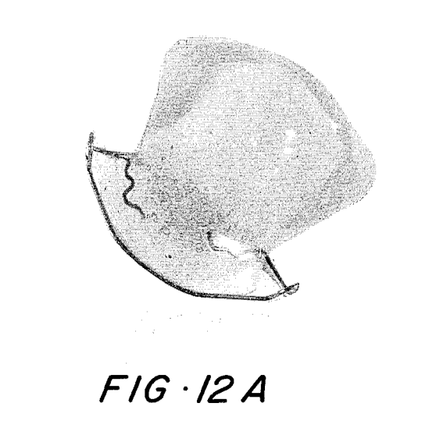
FIGS. 12A and 12B illustrate two separate perspective photographic views of the performed retainer of the present invention in its original state as supplied to the orthodontist before the procedure of fitting it to the patient's mouth has begun.
Figure 12B:
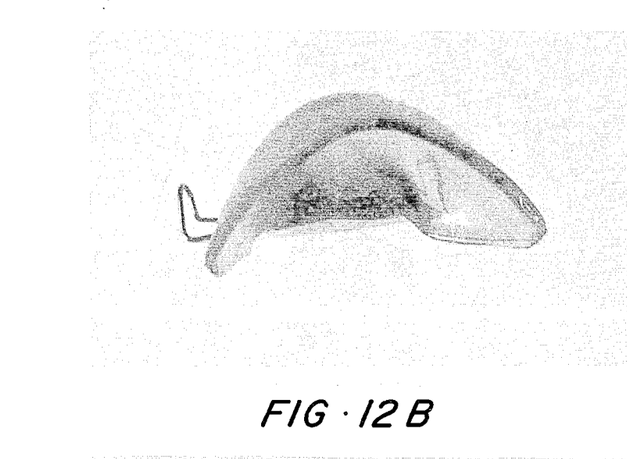

The retainer as shown in FIG. 12 is removed from the box and gently placed in the mouth to check if the size of wire 25 adapts to the mouth properly. This is done by checking to see if when the wire is adapted closely to the four upper incisors the horizontal connecting wire 29 falls within one millimeter of the interproximal between the cuspid and bicuspid (along line W). If the wire approximates itself this way, the plastic mouthpiece will be able to be molded to the palatal anatomy.

Figure 13A:
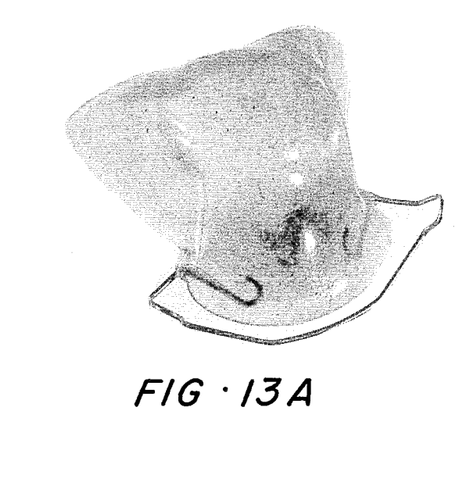
FIGS. 13A and 13B are perspective photographic views similar to FIGS. 12A and 12B but illustrating a retainer after a first stage in the process of fitting the retainer to a patient's mouth.
Figure 13B:
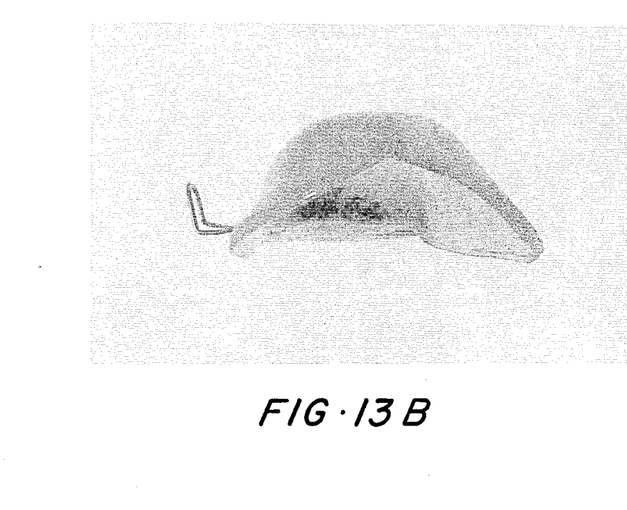
Figure 14A:
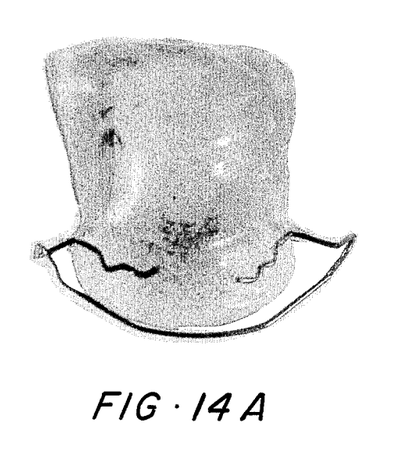
FIGS. 14A and 14B are similar perspective photographic views illustrating a retainer during a subsequent stage in the fitting procedure.
Figure 14B:
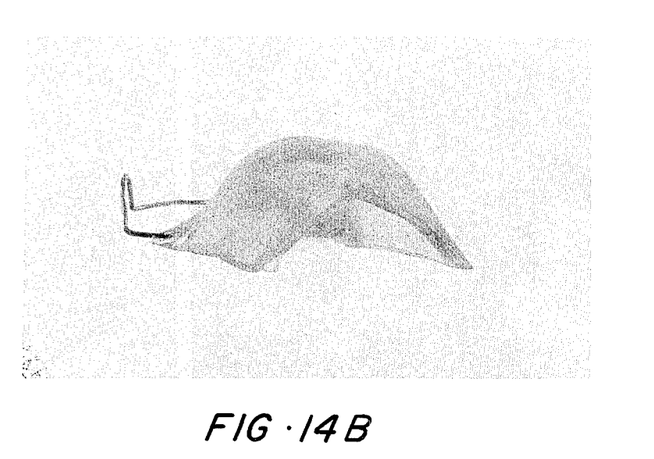

The retainer is heated, e.g. to 180°F – 190°F, and quickly placed into the patient's mouth (or it can be boiled and then held momentarily under cold water then placed into the patient's mouth). The wire is adapted to the interproximal area between the upper laterals and cuspids while firmly pushing and adapting the soft plastic to the palate (that is anterior to the cuspids) superiorly and labially against the anterior teeth. The next step is to adapt the soft plastic next to the palate (distal to the cuspids) superiorly and laterally. The lingual surfaces of the posterior teeth midway between the gingival margin and the occlusal surfaces are marked on the retainer with a grease pencil. FIG. 13 shows the retainer at this stage. The retainer is removed and momentarily held in cold water and the excess material occlusal to the marking is removed with an acrylic bur or on a lathe whereafter the retainer appears as shown in FIG. 14. The retainer is slightly softened once again, particularly in the anterior area 16 and the patient is asked to occlude the teeth and any interferences for a correct bite are removed and the anterior bite plate is adjusted at this time.

Figure 15A:
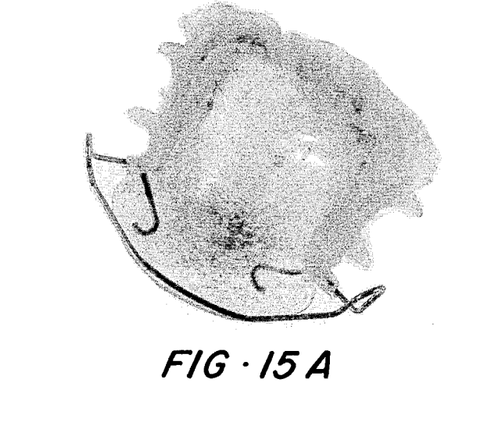
FIGS. 15A and 15B are similar perspective photographic views illustrating the preformed retainer at a stage in the fitting process subsequent to that stage illustrated in FIGS. 14A and 14B.
Figure 15B:
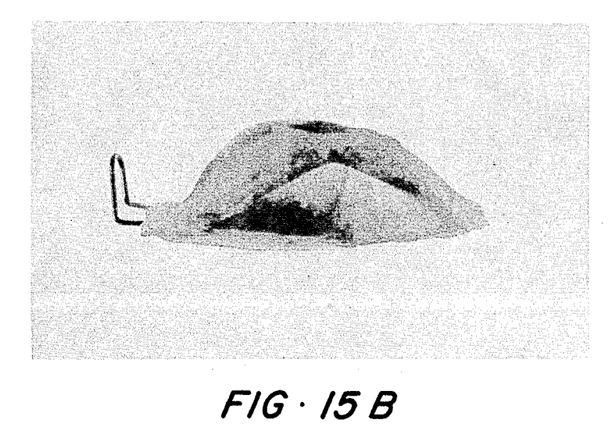

Cold-cure acrylic (acrylic monomer and polymer) is mixed and the tissue surfaces around the gingival area of the posterior teeth on the retainer and across the back of the retainer from one side to the other side are painted with one coat of acrylic self-cure monomer. The soft acrylic is then adapted in the form of a long roll about ⅛ inch in diameter from the bicuspids posteriorly to the most posterior margin of the retainer on both sides and across the back from one side to the other. The retainer is pushed into the mouth and held in place for about one minute. It is then removed and when hard it appears as shown in FIG. 15, after which it is trimmed with an acrylic bur and slightly polished. The retainer is then finished and given to the patient to wear. The finished retainer is shown in FIG. 16.

Figure 16A:
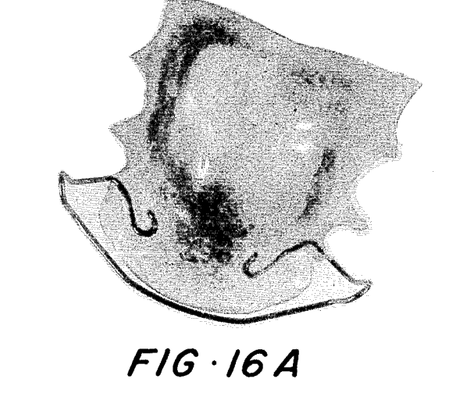
FIGS. 16A and 16B are similar perspective views illustrating the finished retainer fitted to the patient and ready for use.
Figure 16B:
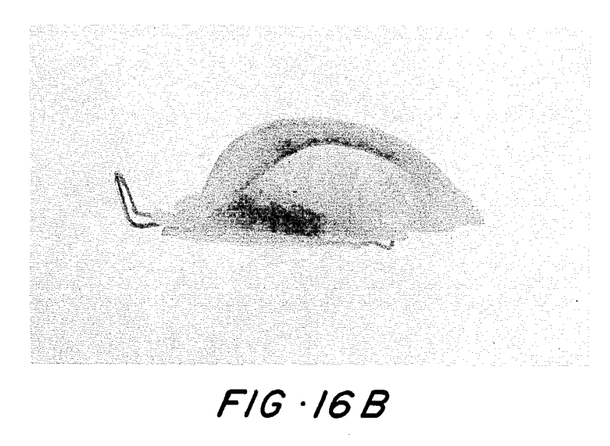
Figure 19:
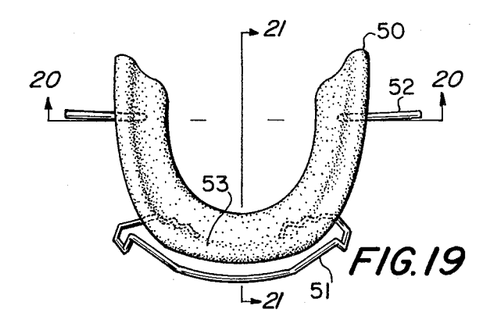
FIG. 19 is a plan view of a preformed retainer constructed in accordance with the present invention and adapted for use with the lower anterior teeth.
Figure 20:
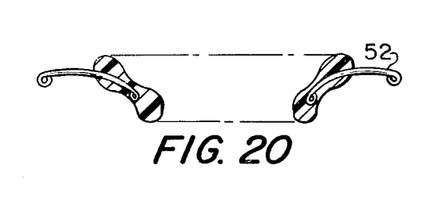
FIG. 20 is a vertical coronal sectional view taken along line 20—20 of FIG. 19.
Figure 21:
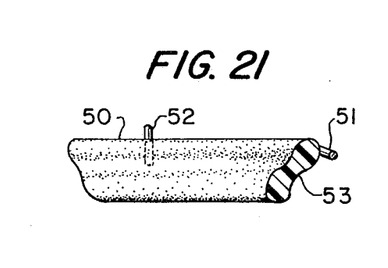
FIG. 21 is a vertical sagittal sectional view taken along line 21—21 of FIG. 19.
Figure 22:
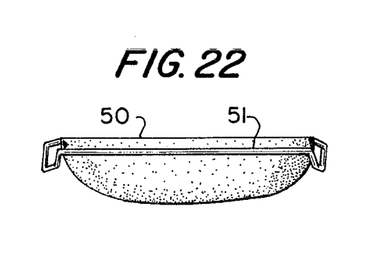
FIG. 22 is a front elevational view of FIG. 19.

In an alternative procedure, rather than use a cold-cure acrylic to form the interproximal points, the plastic of the preform itself may be pushed into the interproximal and trimmed, once again resulting in the same configuration as shown in FIG. 16. This latter procedure has the advantage of being somewhat faster in that it does not involve the use of the cold-cure acrylic. However, it is somewhat more difficult in that it involves the use of a material which have much greater softening capabilities, notwithstanding the fact that it must be sufficiently hard and resistant to warpage at its posterior portion at body temperatures.

Following this alternative procedure, after the retainer has been softened, placed in the mouth and shaped against the anterior, upper and lateral lingual surfaces, the said sides are pushed out against the posterior teeth, particularly at the interproximals. A pencil is used as in the previous example to indicate the level at which the posterior sides are to be cut and at this time the exact position of the interproximals are also marked. The retainer is then removed and held under cold water for a few seconds. The posterior lateral sides are then trimmed with an acrylic bur to the markings. However, at this time the interproximals are preserved and each should come to a sharp point so that they can be bent back into the interproximal spaces, thereby aiding in retention of the retainer within the mouth. The posterior panels or sides are alone heated to 180°F while the rest of the retainer remains cold and stiff. The retainer is then placed back in the mouth a second time and an amalgam plugger is used to bend the sharp pointed interproximal spurs into the interproximal areas between the posterior teeth while the whole lateral sides are held laterally against the teeth. When hard it is removed and again placed in cold water for a few seconds. This completes the alternate formation of the interproximal points. After this the palatal bite shelf is adjusted as in the previous example.

Numerous plastic materials are known which are stiff at body temperature and which can be softened at elevated temperatures, including for example polyurethane, polypropylene, polyethylene, resins and acrylic resins including copolymeric acrylic resins such as methyl methacrylate - butyl acrylate copolymers, methyl methacrylate - vinyl chloride copolymers and the like. A material which has been found particularly suitable for the present invention, however, is a material which is a copolymer of methyl methacrylate and ethyl acrylate. Good results have been achieved with copolymers including 55 to 60% methyl methacrylate, with the remainder being ethyl acrylate. Copolymers having 55% methyl methacrylate to 45% ethyl acrylate soften all the way down to 140° F and can be molded easily by hand at this temperature. To avoid any tendancy to deform at a lower temperature approaching body temperature, one would prefer a higher percentage of methyl methacrylate such as 60% methyl methacrylate to 40% ethyl acrylate as this copolymer would soften and hence be molded easily by hand only down 170° F so that it would be essentially stiffer at body temperature than the above mentioned 55-45% copolymer. In any event, because of the nature of these materials the patient is instructed not to place the retainer directly in sunlight and to keep it away from excess heat, for example in excess of 110° F.

As noted earlier, prior art procedures require approximately one and a half hours of professional time and at least several days are required to completely fabricate the retainer, and the disadvantages associates with these delays has been described above. In contrast thereto, with the present invention, following the alternative procedure of utilizing the material to the preform itself to form the interproximal points takes an absolute total of only ten minutes from the time that the orthodontic appliances such as the braces or the like are removed and the labial retainer is finished and ready for use. The procedure of using the self-cure acrylic to form the interproximal points merely adds another five minutes which still compares quite favorably with the one and a half hours of professional time and the overall delay of severals days in the prior art.

As mentioned above, it is important that the labial wire passes through the proper interproximal groove between the canine and bicuspid teeth. This can easily be accomplished utilizing preferable materials such as those specified above since they are capable of limited stretching so that one can stretch the preform between the wire ends and push the wires into place with an amalgam plugger or with finger pressure, thus providing some degree of latitude to perfect the fitting of the wires to the teeth. If it is found that the material softens or warps in the mouth, the self-cure acrylic mentioned above can be coated over the external surface and this will prevent such warping of the underlying material.

Although the invention has been described in considerable detail with repsect to preferred embodiments thereof, it will be apparent that the invention is capable of numerous modifications and variations apparent to those skilled in the art without departing from the spirit and scope of the invention.

I claim:

1. A preformed orthodontic device adapted to be placed within a patient's mouth and reshaped against the lingual surfaces for holding a wire against the labial surfaces of the patient's anterior teeth, said device comprising:
   a forward portion having a front edge positionable adjacent the lingual surfaces of the said anterior teeth,
   and a rearward portion extending rearwardly along the lingual surfaces of some posterior teeth including at least the bicuspid teeth, said rearward portion including an essentially plain exterior surface lying adjacent said posterior teeth at least from that side of the gingival edges away from the occlusal edges, across the gingival edges to at least part of the distance towards the occlusal edges thereof.

2. A preformed orthodontic device according to claim 1, said rearward portion extending alongside the lingual surfaces beyond the occlusal edges of the posterior teeth.

3. A preformed orthodontic device according to claim 2, said rearward portion extending rearwardly to at least the second molars.

4. A preformed orthodontic device according to claim 1, said device being a maxillary retainer and said rear portion being in the shape of an arch having an upper portion adapted to be shaped against the palate and lateral sides extending alongside said lingual surfaces of some posterior teeth.

5. A preformed orthodontic device according to claim 4, said lateral sides extending along said lingual surfaces of the said posterior teeth to below the occlusal edges thereof.

6. A preformed orthodontic device according to claim 5, said rearward portion extending rearwardly to at least the second molars.

7. A preformed orthodontic device according to claim 1, including a labial wire anchored at its ends within the device and extending about the front of the device for lying against the labial surfaces of said anterior teeth.

8. A preformed orthodontic device according to claim 7, said front portion increasing in thickness just rearward of the front edge to form a thicker part, and said wire being anchored within said thicker part.

9. A preformed orthodontic device according to claim 1, said device being of a material which is sufficiently stiff at body temperature to retain its shape upon normal use and which becomes sufficiently soft at a temperature between 110° F and 190° F to be essentially non-elastically reshaped by hand to the contours of at least some lingual surfaces by hand manipulation while the device is within the patient's mouth.

10. A preformed orthodontic device according to claim 9, said device being a maxillary retainer and said rear portion being in the shape of an arch having an upper portion adapted to be shaped against the palate and lateral sides extending alongside said lingual surfaces of some posterior teeth, and said front portion increasing in thickness just rearward of the front edge to form a thicker part, and wherein at the softening temperature only the said rearward portion is capable of hand manipulation for reshaping to the contours of the lingual surfaces and the said thicker part at the front essentially retains its shape for subsequent use of the device.

11. A preformed orthodontic appliance according to claim 9, wherein the softening temperature is between 140° F and 170° F.

12. An orthodontic device according to claim 9, said front portion increasing in thickness just rearward of the front edge to form a thicker part, and including a labial wire anchored at its ends within the device and extending about the front of the device for laying against the labial surfaces of said anterior teeth, said wire being anchored within the thicker part, and said thicker part being stretchable in said softened state to vary the overall length of the said front curved part of the wire.

13. An orthodontic appliance according to claim 1, said rearward portion extending rearwardly to at least the second molars, and including wire clasps embedded at their inner ends in said rearward portions and extending outwardly to pass between a posterior interproximal and engage on the buccal side of the posterior teeth.

14. A preformed orthodontic device according to claim 1, said device being a mandibular retainer.

15. A preformed orthodontic device according to claim 14, said device being an injection molded device.

16. A preformed orthodontic device adapted to be placed within a patient's mouth and reshaped against the lingual surfaces for holding a wire against the labial surfaces of the patient's anterior teeth, said device comprising:
a forward portion having a front edge positionable adjacent the lingual surfaces of the said anterior teeth, and a rearward portion extending rearwardly along at least some of the lingual surfaces of the teeth rearward of the anterior teeth the thickness of the front portion increasing from a thin front edge to a thicker part just rearwardly thereof, said thicker part being thicker than the said rearward portion,
and a wire anchored at its ends in the said thicker part and protruding out the sides thereof and extending about the front of the device with a curvature which generally parallels that of said front edge for lying against the labial surfaces of said anterior teeth.

17. A preformed orthodontic device according to claim 16, said device being a maxillary retainer, said thicker part shaped to engage and fit against the surface of the palate of the patient immediately rearward of said front edge.

18. A preformed orthodontic device according to claim 17, the ends of the wire being located approximately halfway through the thickness of the said thicker part.

19. A preformed orthodontic device according to claim 16, said rearward portion extending rearwardly along the lingual surfaces of at least the bicuspid teeth, said rearward portion including an essentially plain exterior surface lying adjacent said posterior teeth at least from that side of the gingival edges away from the occlusal edges, across the gingival edges to at least part of the distance toward the occlusal edges thereof.

20. A preformed orthodontic device according to claim 19, said rearward portion extending alongside the lingual surfaces beyond the occlusal edges of the posterior teeth and extending rearwardly at least to the second molars.

21. A preformed orthodontic device according to claim 19, said device being of a material which is sufficiently stiff at body temperature to retain its shape upon normal use and which becomes sufficiently soft at a temperature between 110° F and 190° F to be essentially non-elastically reshaped by hand to the contours of at least some lingual surfaces by hand manipulation while the device is within the patient's mouth.

22. A preformed orthodontic device according to claim 16, said device being a mandibular retainer.

23. A preformed orthodontic device according to claim 16, the ends of said wire being connected to form a closed loop which passes through said thicker part of the front portion.

24. A preformed orthodontic device adapted to be placed within a patient's mouth and reshaped against the lingual surfaces for holding a wire against the labial surfaces of the patient's anterior teeth, said device comprising:
a forward portion having a front edge positionable adjacent the lingual surfaces of the said anterior teeth,
and a rearward portion extending rearwardly alongside at least some of the lingual surfaces rearward of the anterior teeth and of a shape different from the precise contour of the lingual tooth or tissue surfaces of any specific patient,
said device being of a material which is sufficiently stiff at body temperature to retain its shape upon normal use and which becomes sufficiently soft at temperature at least 10° F above body temperature but less than 190° F that at least the said rearward portion can be reshaped to the contours of certain lingual surfaces by hand manipulation while within the patient's mouth and then essentially maintain that shape upon returning to body temperature.

25. A preformed orthodontic device according to claim 24, wherein said material softens between 140° F and 170° F.

26. A preformed orthodontic device according to claim 24, said rearward portion having an essentially plain surface facing the said lingual surfaces of the posterior teeth and being capable of being reshaped against the lingual surfaces when the material is softened.

27. A preformed orthodontic device according to claim 24, said front portion increasing in thickness just rearward of the front edge to form a thicker part, and wherein at the softening temperature only the said rearward portion is capable of hand reshaping, the said thicker part at the front essentially retaining its shape for subsequent use of the device.

28. A preformed orthodontic device according to claim 27, including a labial wire anchored at its end within the device and extending about the front of the device for lying against the labial surfaces of said anterior teeth, the said wire being anchored within said thicker part, and said thicker part being stretchable at said softening temperature to vary the overall length of the said front curved part of the wire.

29. A preformed orthodontic device according to claim 24, said device being a maxillary retainer and said rear portion being in the shape of an arch having an upper portion adapted to be shaped against the palate and lateral sides extending alongside said lingual surfaces of some posterior teeth.

30. A preformed orthodontic device according to claim 29, said front portion increasing in thickness just rearward of the front edge to form a thicker part, and wherein at the softening temperature only the said rearward portion is capable of hand reshaping, the said thicker part at the front essentially retaining its shape for subsequent use of the device.

31. A preformed orthodontic device according to claim 30, including a labial wire anchored at its ends within the said thicker part of the device and extending about the front of the device for lying against the labial surfaces of said anterior teeth, and said thicker part being stretchable at said softening temperature to vary the overall length of the said front curved part of the wire.

32. A preformed orthodontic device according to claim 24, said device being a mandibular retainer.

33. A set of a plurality of preformed orthodontic devices of the type adapted to be placed within a patient's mouth and reshaped against the lingual surfaces for holding a wire against the labial surfaces of the patient's anterior teeth:
each device of the set including a forward portion having a front edge positionable adjacent the lingual surfaces of the anterior teeth and a rearward portion extending rearwardly alongside at least some of the lingual surfaces rearward of said anterior teeth, the shape of the rearward portion being different from the precise contour of the said lingual surfaces of any specific patient, the device being of a material which under at least some conditions permits essentially non-elastic reshaping of the device within the patient's mouth to adapt it to the shape of certain adjacent lingual surfaces of the patient,
each device of the set being of a different size from the other devices of the set for fitting a different range of mouth sizes, and all devices of the set, taken together, fitting substantially all mouth sizes of the total dental population.

34. A set of preformed orthodontic devices according to claim 33, wherein there are seven different sizes in the set, which set fits approximately 95% of the entire dental ptaient population.

35. A set of preformed orthodontic devices according to claim 34, wherein said devices are maxillary retainers and include labial wires embedded therein.

36. A set of preformed orthodontic devices according to claim 35, said devices having dimensions substantially as set forth in Tables I-X.

37. A set of preformed orthodontic devices according to claim 35, wherein the radius of curvature of the labial wires of all devices of the set are essentially 0.868 inches.

38. A set of preformed orthodontic devices according to claim 35, wherein the total mesio-distal measurement along the front of the devices between the points where the wires enter the devices to be held therein is approximately 42.5 mm for the smallest size and 60.5 mm for the largest size.

39. A set of preformed orthodontic devices according to claim 35, said devices having dimensions substantially as set forth in Table I.

40. A set of preformed orthodontic devices according to claim 35, said devices having dimensions substantially as set forth in Table II.

41. A set of preformed orthodontic devices according to claim 35, said devices having dimensions substantially as set forth in Table III.

42. A set of preformed orthodontic devices according to claim 35, said devices having dimensions substantially as set forth in Table IV.

43. A set of preformed orthodontic devices according to claim 35, said devices having dimensions substantially as set forth in Table V.

44. A set of preformed orthodontic devices according to claim 35, said devices having dimensions substantially as set forth in Table VI.

45. A set of preformed orthodontic devices according to claim 35, said devices having dimensions substantially as set forth in Table VII.

46. A set of preformed orthodontic devices according to claim 35, said devices having dimensions substantially as set forth in Table VIII.

47. A set of preformed orthodontic devices according to claim 35, said devices having dimensions substantially as set forth in Table IX.

48. A set of preformed orthodontic devices according to claim 35, said devices having dimensions substantially as set forth in Table X.

49. A set of preformed orthodontic devices according to claim 33, each said device being of a material which is sufficiently stiff at body temperature to retain its shape upon normal use and which becomes sufficiently soft at a temperature between 110° F and 190° F to be essentially non-elastically reshaped by hand to the contours of at least some lingual surfaces by hand manipulation while the device is within the patient's mouth.

50. A set of preformed orthodontic devices according to claim 49, said rearward portion of each device having an essentially plain surface facing the said lingual surfaces of the posterior teeth and being capable of being reshaped against the lingual surfaces when the material is softened.

51. A set of preformed orthodontic devices according to claim 50, the front portion of each device increasing in thickness just rearward of the front edge to form a thicker part, and wherein at the softening temperature only the said rearward portion is capable of hand reshaping, the said thicker part at the front essentially retaining its shape during subsequent use of the device.

52. A set of preformed orthodontic devices according to claim 51, including a labial wire anchored at its ends within each device and extending about the front of its respective device for lying against the labial surfaces of said anterior teeth, said wires being embedded in the said thicker part.

53. A set of preformed orthodontic devices according to claim 52, each device being a maxillary retainer and said rear portion being in the shape of an arch having an upper portion adapted to be shaped against the palate and lateral sides extending alongside said lingual surfaces of some posterior teeth.

54. A method of fitting a patient with an orthodontic device of the type which is placed in the patient's mouth against the lingual surfaces for holding a wire against the labial surfaces of said anterior teeth, comprising the steps of:

taking a device which is preformed, prior to any contact with the mouth any specific patient or any facsimile thereof, to include at least a front portion positionable adjacent the lingual surfaces of the anterior teeth for cooperating in use of the device with a wire located on the labial side of the anterior teeth, and a rearward portion extending rearwardly along the lingual surfaces rearward of the anterior teeth, inserting the device into the mouth against the said lingual surfaces, and while the device is in the mouth, essentially non-elastically reshaping the device to the contours of at least some of said lingual surfaces to retain the device in the patient's mouth during normal use thereof.

55. A method according to claim 54, wherein there are provided a limited number of said preformed devices which are different from each other and which together fit substantially the entire dental patient population, and said step of taking further including measuring the patient's mouth and, depending on said measurement, selecting an appropriate size preformed device.

56. A method according to claim 54, wherein the device is of a material which softens at a temperature between 110° and 190° F and the device includes a labial wire anchored at its ends in the front portion, and said inserting step includes heating the device to soften it and while soft, placing the labial wire against the labial surfaces of the front teeth and with the labial wire in place manipulating the forward and rearward portions of the device to adapt them to at least some of the lingual surfaces.

57. A method according to claim 56, wherein the device is a maxillary retainer, and said step of manipulating includes shaping the rearward portion to the palate and the lateral lingual surfaces.

58. A method according to claim 57, including cutting the rearward portion after it has been shaped to the palate and lingual surfaces approximately just occlusal of the gingival edges of the posterior teeth.

59. A method according to claim 58, including forming interproximal points along the outer edges of the cut rearward portion by bending parts of said edges into the interproximals between the posterior teeth.

60. A method according to claim 58, including forming interproximal points along the cut outer edges of the rearward portion by adding a self-cure material to the said outer edges and placing the device into the patient's mouth so that the self-curing material in its softened state forms to the shapes of the interproximals and then permitting such self-curing material to harden.

61. A method according to claim 57, including adding a self-cure material along the posterior end of the retainer to prevent warpage thereof.

62. A method according to claim 56, wherein the device is heated to a temperature between 140° and 170° F to soften the same.

63. A method according to claim 54, wherein the individual preformed devices are made by injection molding.

* * * * *